(12) United States Patent
Breen et al.

(10) Patent No.: US 6,318,158 B1
(45) Date of Patent: Nov. 20, 2001

(54) SAMPLE PREPARATION AND DELIVERY SYSTEM EMPLOYING EXTERNAL SONICATOR

(75) Inventors: Thomas Breen; Mark M. Beaulieu, both of Coral Springs; Enrique Rodriguez, Hialeah; Arys S. Cuervo, Miami, all of FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/516,693

(22) Filed: Mar. 1, 2000

(51) Int. Cl.[7] .................................................... G01N 35/04
(52) U.S. Cl. .................. 73/64.56; 73/863.01; 422/128
(58) Field of Search .................... 73/64.56, 432.1, 73/863.01; 422/128; 204/157.42, 157.62

(56) References Cited

U.S. PATENT DOCUMENTS

| | | | | |
|---|---|---|---|---|
| 4,071,225 | * | 1/1978 | Holl | 366/114 |
| 4,528,159 | * | 7/1985 | Liston | 422/65 |
| 4,914,966 | * | 4/1990 | White, Jr. et al. | 73/863.01 |
| 4,930,898 | * | 6/1990 | Miller-Ihli | 363/109 |
| 5,380,487 | * | 1/1995 | Choperena et al. | 422/63 |
| 6,079,508 | * | 6/2000 | Caza | 175/66 |
| 6,118,541 | * | 9/2000 | Mizzer et al. | 356/142 |

FOREIGN PATENT DOCUMENTS

02043000 * 2/1990 (JP) ............................................. 96/1

* cited by examiner

Primary Examiner—Hezron Williams
Assistant Examiner—Michael Cygan
(74) Attorney, Agent, or Firm—Charles E. Wands; Mitchell E. Alter (57) ABSTRACT

A particulate sample mixing and delivery apparatus externally sonically mixes respective samples of particulate stored in storage containers that are sequentially indexed by a carousel prior to being dispensed into an analyzer reservoir. Each container is compliant to acoustic energy emitted by a sonicator unit that is placed against an external surface of a respective container to which preferably a carrier fluid and surfactant are controllably supplied. After sonication, the container is indexed to a sample dispensing location adjacent to the analyzer reservoir. A tiltable cradle then rotates the container to rapidly dispense its mixed contents into the reservoir, and then discards the empty container.

19 Claims, 8 Drawing Sheets

SAMPLE PREPARATION AND DELIVERY SYSTEM EMPLOYING EXTERNAL SONICATOR

FIELD OF THE INVENTION

The present invention relates in general to sample analysis, such as, but not limited to systems for conducting particle size measurements, and is particularly directed to a new and improved sample preparation and delivery apparatus that is operative to controllably sonically mix, and deliver the contents of samples, such as particulates, stored in containers, that are transported by a controllably indexed conveyor to the input reservoir of an associated sample analysis system.

BACKGROUND OF THE INVENTION

Systems employed for particulate sample analysis, such as, but not limited to, those employed in medical and industrial applications to analyze particles in raw materials used to develop final products, customarily include, or are coupled with, some form of sample delivery and mixing apparatus, that 'prepares' a respective sample, namely, places it in the physical condition necessary for acceptance and processing through the analyzer. Typically, preparation of a particulate sample involves suspending and separating the particles in a prescribed fluid carrier (such as an aqueous solution), which is then injected into a fluid transport channel for delivery to a particle measurement (e.g., optical illumination-based) subsystem.

Figure 1:
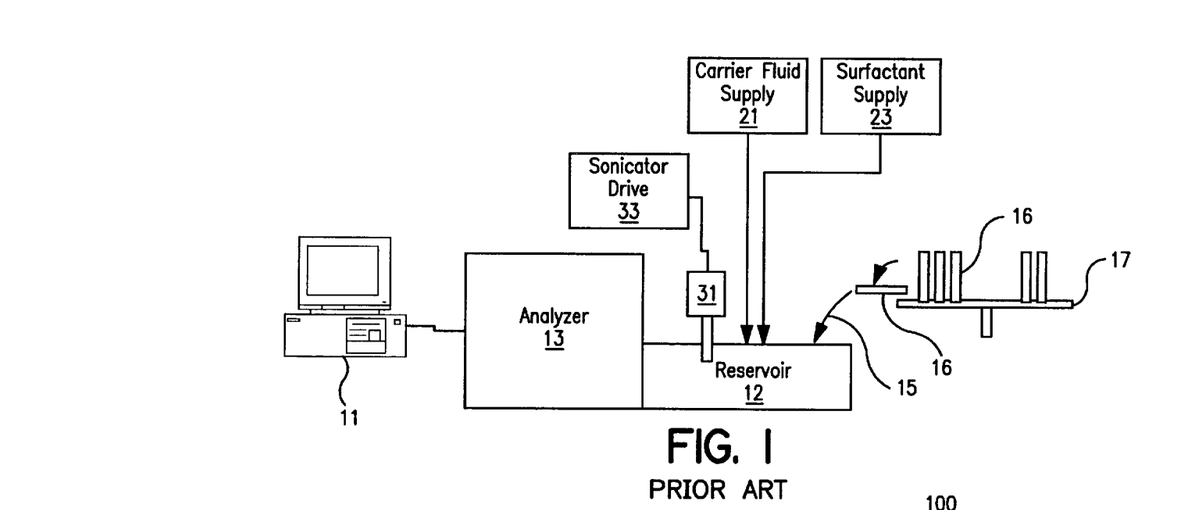
FIG. 1 diagrammatically illustrates a conventional sample delivery and mixing apparatus according to the prior art.

For this purpose, as diagrammatically illustrated in FIG. 1, the front end of a sample analyzer 13, having an associated computer workstation 11, includes an input reservoir 12 to which a respective sample 15 is dispensed (for example by way of a sample-retaining test cup, tube or the like 16 to the reservoir by way of a conveyor 17). In order to place the sample particles in a solution for analysis, the reservoir is supplied from a carrier fluid source 21 with a carrier fluid into which the sample is to be mixed, and from a surfactant source 23 with a surfactant that serves to disperse the particles of the sample 15 within the carrier.

A sonic probe (or sonicator) 31 is inserted into the reservoir 12 and which is then stimulated by an ultrasonic drive signal from an energization source 33, so as to cause a sonically induced agitation of the combination of carrier fluid, sample and surfactant. This sonic mixing operation is intended to thoroughly separate and suspend the sample particles in the carrier fluid, so that the mixed contents of the reservoir are in the appropriate physical state required by the sample analyzer 13. Once the analysis has been completed, the reservoir and fluid flow path through the analyzer are subjected to a purging rinse, in preparation for the next sample.

Unfortunately, there are a number of problems associated with such a conventional sample-preparation configuration. One of the most significant is the fact that the sonicator is actually immersed into the fluid contents of the reservoir. Because the volume of the reservoir is relatively large, the sonic energy emitted by the probe is reduced as it diffuses into the contents of the reservoir. This means that a relatively large amount of probe drive energy is necessary to obtain thorough mixing of the sample in the carrier, resulting in poor efficiency of the sonicator operation.

In addition, because the probe is immersed into the mixture, it not only may displace some of the sample, but itself becomes coated with sample and surfactant, and therefore requires cleaning after each use. Moreover, depending upon the application, the mixture into which the probe is inserted may be corrosive to the probe, which shortens the life of the probe.

SUMMARY OF THE INVENTION

In accordance with the present invention, these and other shortcomings of conventional sample delivery and mixing devices are substantially reduced or effectively eliminated by a sample mixing and delivery apparatus, that is configured to thoroughly sonically prepare (mix) each sample, such as a sample containing one or more particulates, to be analyzed in its own storage container (e.g., test tube) prior to being dispensed into the analyzer reservoir, and without having to insert the sonicator probe into the sample.

For this purpose, a controllably indexed conveyor, such as a carousel, is operative to retain and transport a plurality of sample containers. The sample containers (such as test tubes) are made of a material, such as an elastically deformable transparent plastic, and the like, that is compliant to acoustic energy emitted by a sonicator probe tip placed directly against or in intimate contact with the exterior of the test tube wall. In a non-limiting, but preferred embodiment, the carousel includes a slotted disk that is controllably rotationally indexed by a releasable clutch.

The clutch may include a plurality of ball bearings sized to releasably engage depressions in the carousel disk. In the event of an impairment, the carousel disk will ride up over the ball bearings and slip on the clutch, thereby preventing damage, or injury to the user. The carousel disk also includes a mechanically encoded surface structure, configured to interface with a set of indexing sensors, which provide output signals to a supervisory system controller.

A radially translatable sonicator unit is supported beneath the carousel disk and includes a generally longitudinal probe element. A controllably mechanical bias arrangement is coupled to the sonicator unit and serves to urge or bias the sonicator unit in a radially outward direction toward or away from the center of the carousel and toward its cylindrical periphery. Outward biasing displacement of the sonicator brings the distal end of the probe into intimate contact with the lower portion of a sample-containing test tube, that has been indexed by the carousel disk to a 'mixing' location associated with a 'filling' station directly opposite the sonicator unit.

The apparatus optionally includes a 'filling' station containing a carrier fluid and surfactant supply unit, that is operative to controllably dispense a measured quantity of fluid and surfactant into a respective test tube, that has been rotationally indexed by the carousel to the filling station in preparation for sonication of the sample according to the prior art.

The filling station operates to dilute the sample with a carrier fluid sufficient for effective sonication, which disperses particles of the sample for analysis. As appreciated by one skilled in the art, if the sample is a solution, which contains liquid sufficient for effective sonication, carrier fluid will not need to be added to the sample solution. Moreover, the carrier fluid can comprise a surfactant solution, which facilitates the separation of particles in the sample. Preferably, the carrier solution dilutes the sample to form a sample solution, and a surfactant is added to the sample solution. After dispensing any carrier and/or surfactant by the supply unit, and with the sonicator probe biased into intimate contact with the lower portion of the test tube, the sonicator is energized.

Because the test tube is made of a material that is compliant to acoustic energy emitted by the sonicator unit, and with the sonicator probe tip being urged against a generally lower portion of the test tube where the sample contents tend to gravitate, the sonic energy emitted by the sonicator probe is efficiently transmitted through the sidewalls of the test tube, and effectively concentrated upon that volume of the test tube containing the particulate of the sample. This provides for maximum efficiency particle separation and rapid mixing of the sample, surfactant and carrier fluid.

This substantially improved efficiency of acoustic energy coupling of the external sonicator of the invention means that the amount of sonicator drive energy required to achieve through mixing of the sample can be significantly reduced, in comparison with the relatively poor efficiency of the immersed probe approach of the prior art, described above. Moreover, since the sonicator of the invention is not immersed into the sample, it does not displace any of the contents of the test tube, and cannot become coated or contaminated thereby. Therefore, the life of the probe is substantially improved, as the probe can be repeatedly reused for successively indexed tube samples, without servicing.

After the fill and sonication mix operations carried out at the filling station are completed, the sonicator is moved away from contact with the test tube. The carousel is then indexed to bring the sonicated tube to a sample dispensing position downstream of the filling station. The sample dispensing position includes a tiltable capture cradle adjacent to the input reservoir of the particulate sample analyzer. Alternatively, a sample aspirating station can be used to withdraw the mixed sample from the tube.

The tiltable capture cradle is configured to receive a test tube in its vertical orientation from the carousel and rotates the test tube to the sample dispensing position in a tilted, generally upside down orientation, for dispensing the sonicated contents of the tube. Coupled with the top end of the tiltable capture cradle adjacent the open end of the test tube is a rinse unit, that may be controllably operated while the tube is in its tilted, dispensing orientation above the reservoir, to provide an auxiliary carrier 'flush', and thereby ensure that the entire contents of the tube are completely dispensed. After the sample dispensing operation, the tiltable capture cradle is returned to its vertical orientation, which allows the empty test tube to drop through a trap door into a suitable collection or discard container.

DETAILED DESCRIPTION

Figure 2:
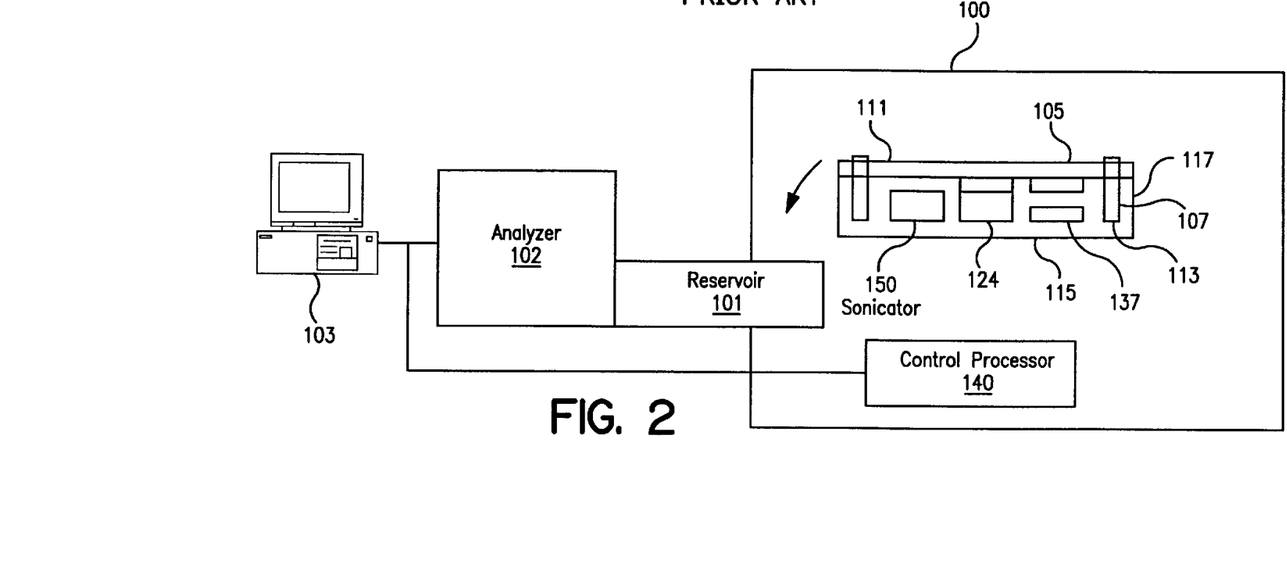
FIG. 2 diagrammatically illustrates the overall architecture of a particulate sample mixing and delivery apparatus in accordance with the present invention.

FIG. 2 diagrammatically illustrates the overall architecture of a particulate sample mixing and delivery apparatus 100 in accordance with the present invention, that is arranged to store, controllably mix and deliver fluid carrier suspended samples of particulate to the sample reception and storage reservoir 101 of a particulate sample analyzer 102, having an associated computer workstation 103. For this purpose, and as shown in greater diagrammatic detail in the plan view of FIG. 3 and the side view of FIG. 4, a controllably rotatable multi-container supporting conveyor 105, preferably configured as a carousel, is configured to support a plurality of sample containers 107, such as plastic test tubes or the like, in a vertical orientation in respective slots 109 adjacent to the peripheral edge 110 of a generally circular carousel disk 111. The test tubes 107 are captured by the disk, such that the bases 113 of the test tubes rest and slide upon the floor 115 of a generally cylindrical carousel support pan 117. As described briefly above, the sample containers (test tubes) 107 are made of a material, such as a compliant transparent plastic, and the like, that is compliant to acoustic energy emitted by a launch probe or transducer placed directly against or in intimate contact with the exterior of the test tube wall. As a non-limiting example, the sample containers may comprise polycarbonate.

Figure 4:
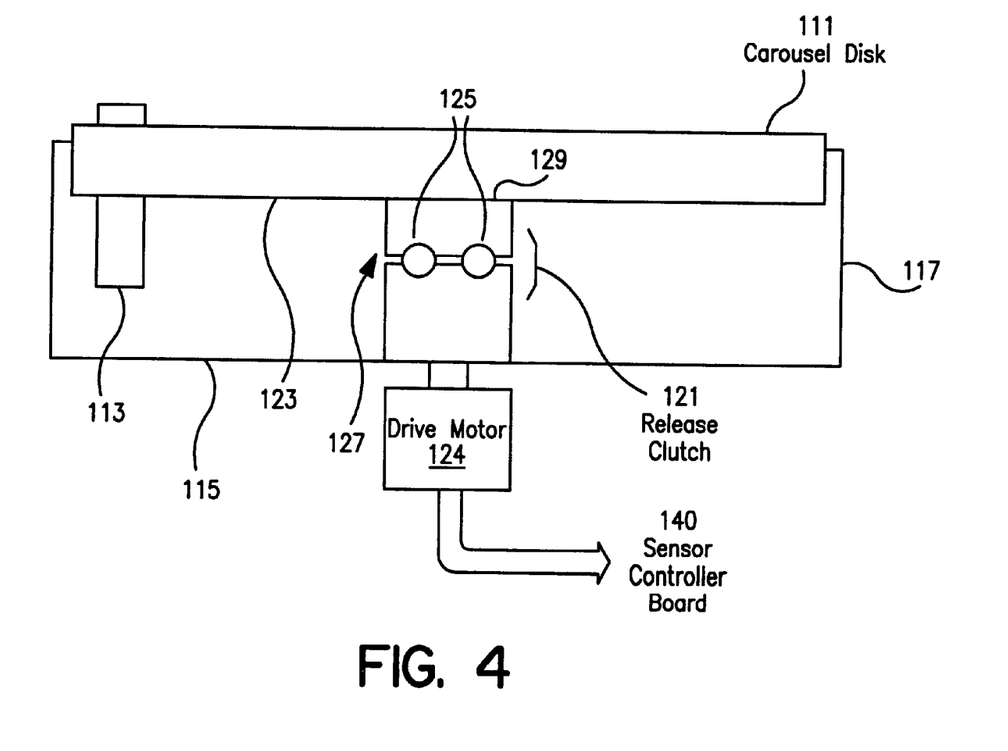
FIG. 4 is a diagrammatic side view of a test tube carousel conveyor, showing a release clutch thereof.

The carousel disk 111 may be controllably driven (rotationally stepped or 'indexed') by a releasable clutch 121 that engages the underside 123 of the disk. For this purpose, the releasable clutch 121 may include a plurality of ball bearings 125 or the like that are sized to fit within and engage corresponding hemispherical depressions 127 formed in a generally central region 129 of the underside of the carousel disk. The carousel disk 111 rests upon the clutch, so that rotating the clutch by an associate carousel drive motor 124, in turn, rotates the carousel. In the event of an impairment, such as an improperly oriented test tube, or a technician's hand, for example, the carousel disk 111 will ride up over the ball bearings 125 and slip on the clutch, thereby preventing damage, or injury to the user.

Figure 3:
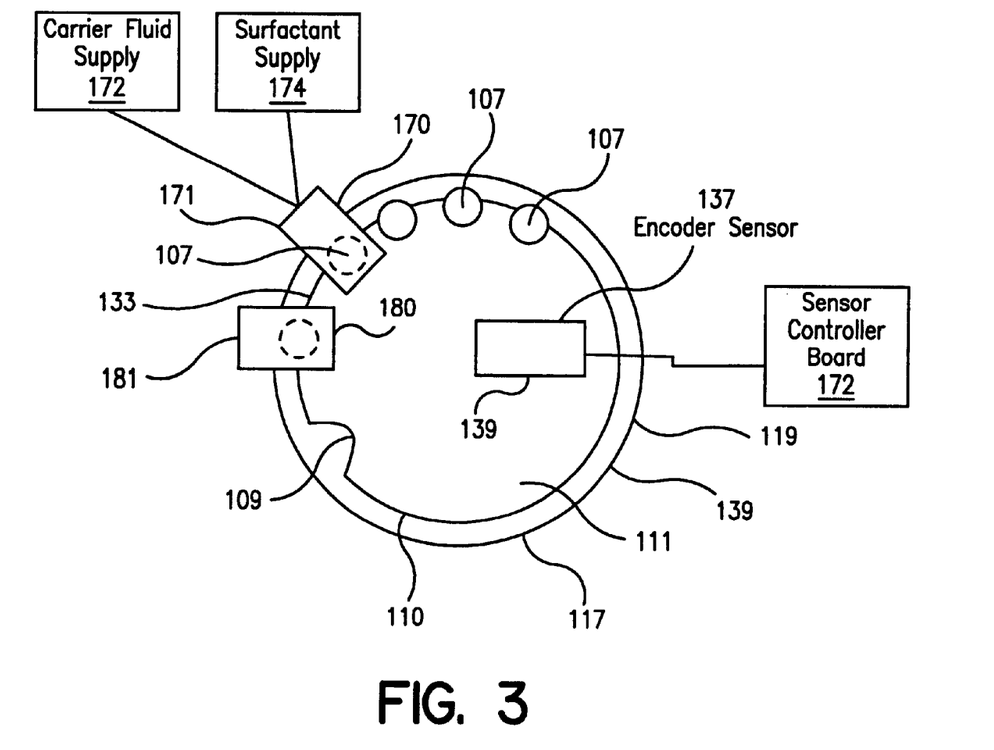
FIG. 3 is a diagrammatic plan view of the particulate sample mixing and delivery apparatus employed in the system of FIG. 2.
Figure 5:
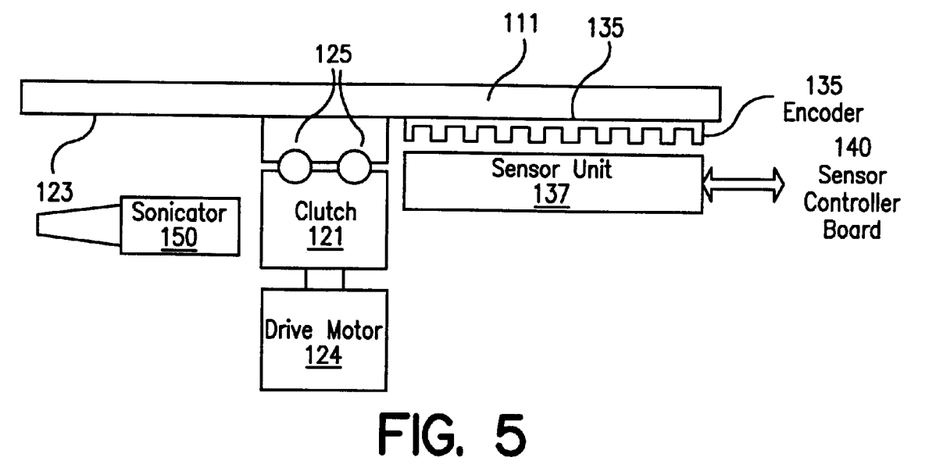
FIG. 5 is a diagrammatic side view of a test tube carousel conveyor, showing its mechanically encoded surface structure interfacing with indexing sensors.

As shown diagrammatically in the plan view of FIG. 3 and in the further side view of FIG. 5, a sector portion 133 of the underside 123 of the carousel disk 111 may also be contoured with a mechanically encoded surface structure 135, that is configured to interface with a set of indexing sensors 137, such as opto-electric devices, or the like, that are supported at a first radial region 139 of the floor 115 of the carousel's support pan 117 between the clutch 121 and the support pan's cylindrical sidewall 119. The outputs of the indexing sensors 137 are monitored by a sensor-controller board 140 for use by a supervisory system controller, which controls various operations of the analyzer. Impairment of rotation of the carousel that causes the disk 111 to slip on the clutch, as described above, will interrupt the mutual coupling between the encoded surface structure 135 and the indexing sensors 137, causing a change in state of the indexing sensor outputs, and informing the system controller of a potential jam problem. In response, the controller may deenergize the carousel drive motor and generate an alarm signal to alert the user of the drive impairment.

Figure 6:
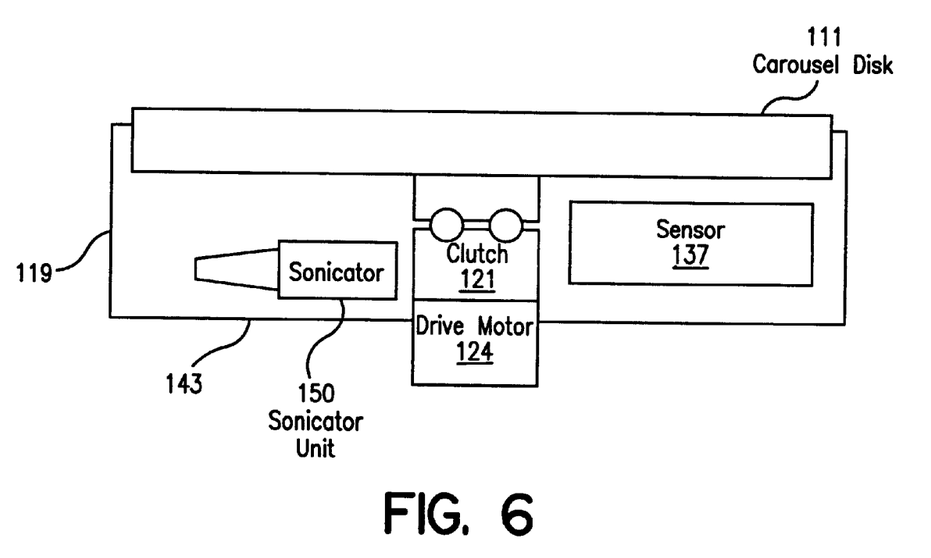
FIG. 6 is a diagrammatic side view of a test tube carousel conveyor, showing the mounting of the sonicator beneath the carousel disk.

As further shown in greater diagrammatic detail in the reduced complexity side view of FIG. 6, a sonicator unit 150 is supported at a second radial region 143 of the floor 115 of the carousel's support pan 117 between the clutch 121 and the support pan's cylindrical sidewall 119. As shown in the diagrammatic plan view of FIG. 7, and the operational side views of FIGS. 8 and 9, the sonicator unit 150 includes a generally radially oriented, longitudinal sonicator probe element 151, that extends from an associated drive unit 152. A sonicator unit of the type shown and described herein may comprise a sonicator unit manufactured by Sonics and Materials, Inc.

Figure 7:
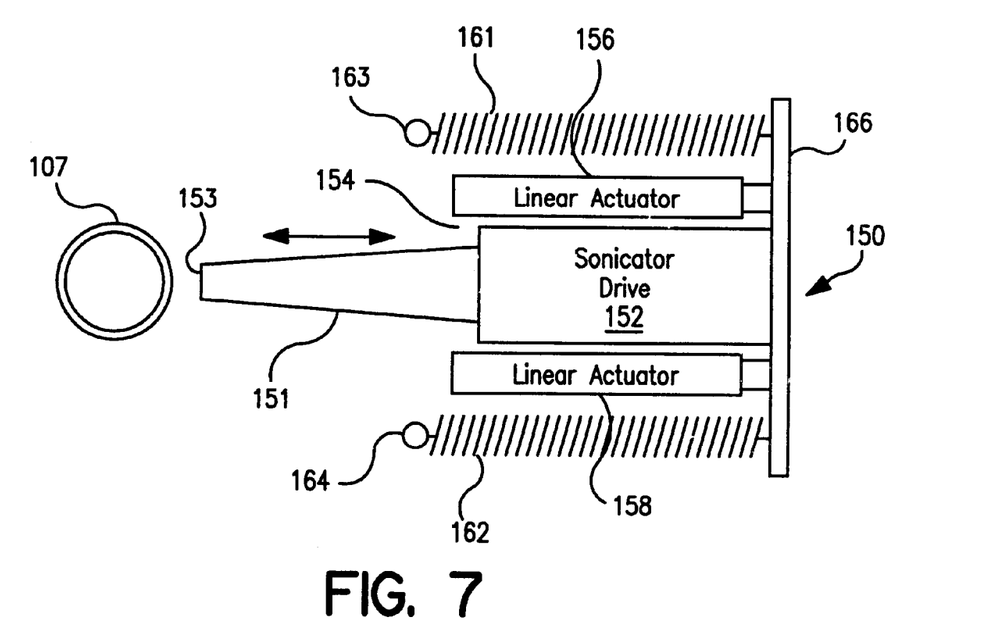
FIG. 7 is a diagrammatic plan view of a sonicator unit.

The distal or acoustic launch tip 153 of the sonicator probe 151 is preferably contoured to conform with the external surface of the sample container against which the probe will be urged when sonicating the sample in its storage container. For the presently described, non-limiting example of a cylindrical test tube to supply the sample, the distal end 153 of the sonicator probe 151 has a generally flat surface that meets or is intimate physical contact with the cylindrical surface of the test tube.

The sonicator 150 is retained in a radial slot 154 formed between a pair of generally longitudinal linear translation units 156 and 158 (such as solenoid actuators), that are fixedly mounted at the floor 115 of carousel support pan 117. A pair of tension springs 161, 162 are retained between respective fixation points 163, 164 at the floor 115 of the carousel support pan 117, and a bar element 166 that is coupled to the sonicator unit 150 and engaged by the linear translation drive units 156, 158. Except during sonication, for example, during rotation of the carousel, linear translation units 156 and 158 are in the energized state, shown in FIG. 8, so as to displace the bar element against the springs 161, 162 and thereby linearly translate the sonicator unit 150 in a radially inward direction toward the center of the carousel and away from the cylindrical sidewall 119 of the support pan 117.

Figure 8:
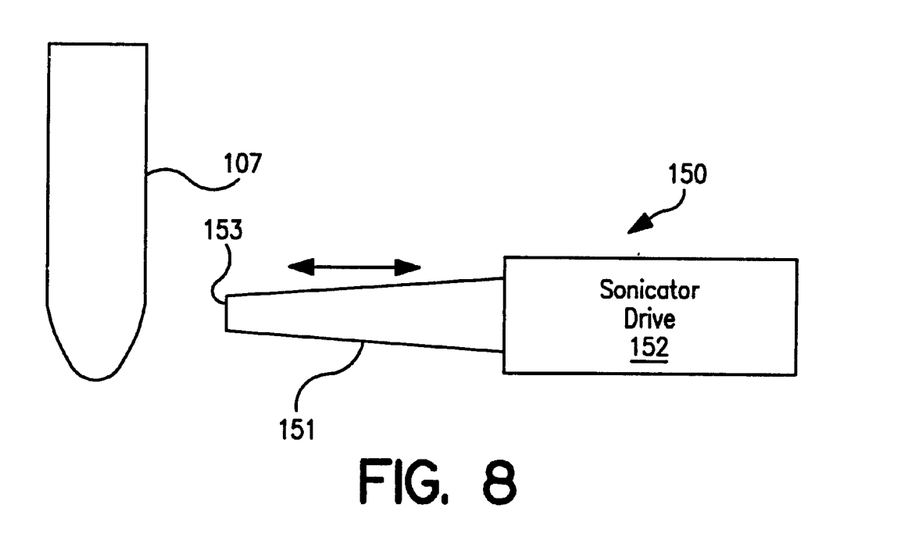
FIGS. 8 and 9 are diagrammatic side views associated with the operation of a sonicator unit.

This inward displacement of the sonicator moves the distal end or tip 153 of the sonicator probe 151 away from, and prevents it from contacting, test tubes 107 retained by the carousel disk as the carousel is rotated. However, when the linear translation units 156 and 158 are deenergized, their associated tension springs 161, 162 urge the sonicator unit 150 in a radially outward direction away from the center of the carousel and toward its cylindrical periphery.

Figure 9:
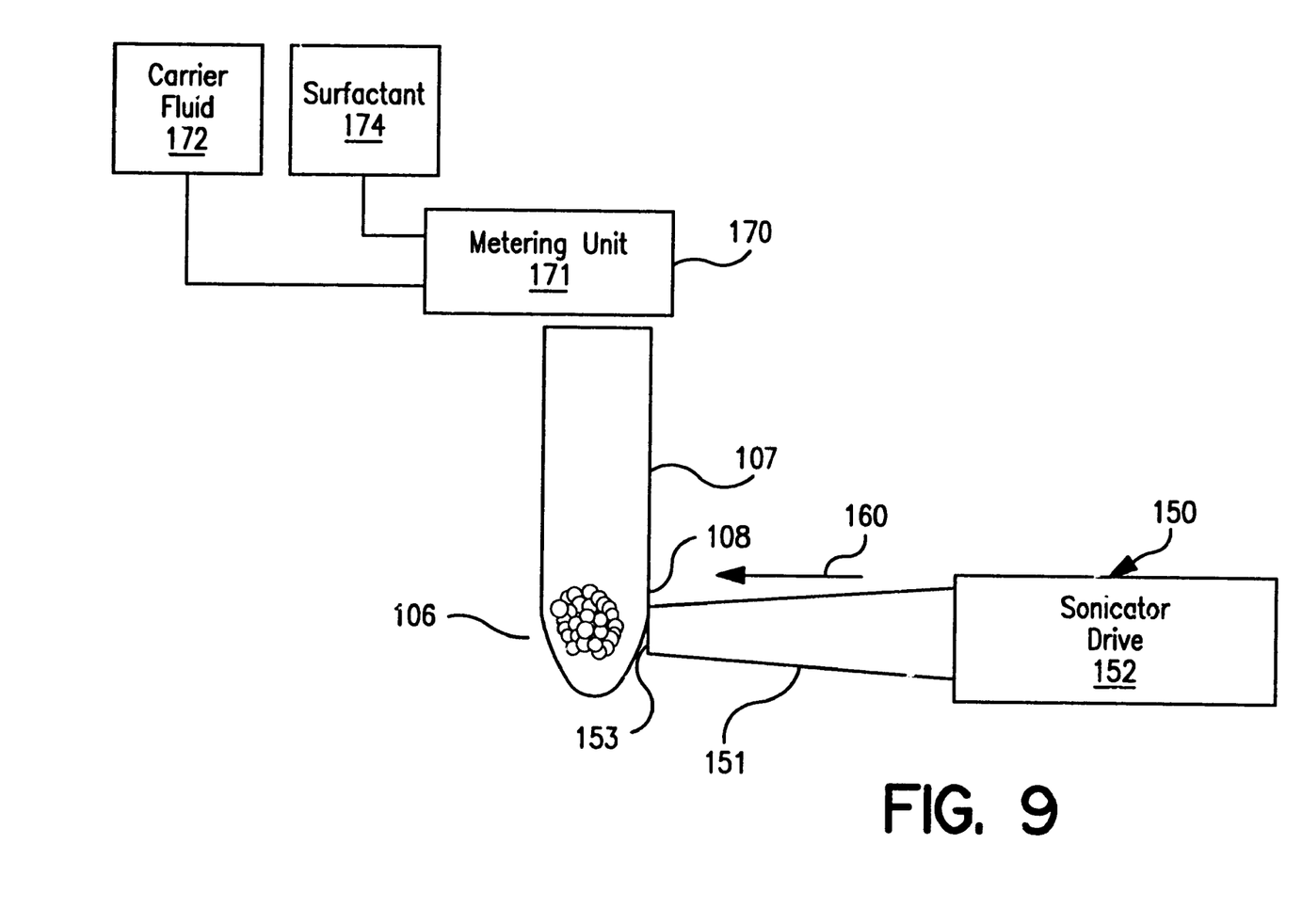

As shown in FIG. 9, this radially outward spring bias (represented by arrow 160) is such as to bring the distal end or tip 153 of the sonicator probe 151 into intimate contact with a lower portion 108 of the external surface of a sample-containing test tube 107. This physical engagement of the sonicator probe tip and the test tube is carried out once the test tube 107 to be sonicated has been indexed by the carousel disk 111 (FIG. 3) to a 'mixing' location associated with a 'filling' station 170 directly opposite to the distal end 153 of the sonicator unit's probe 151.

As further shown in the plan view of FIG. 3 and the side view of FIG. 9, the 'filling' station 170 includes a metering unit 171 that is coupled to a supply of carrier fluid 172 and to one or more sources of surfactant 174. The metering unit 171 is operative, under processor control, to controllably dispense a measured quantity of fluid and surfactant into a respective test tube 107, that has been rotationally indexed by the carousel 105 to the mixing location in preparation for sonication of the sample. After dispensing any carrier and/or surfactant by the metering unit 171, and with the linear translation units 156 and 158 deenergized (which allows the tension springs 161, 162 to urge the sonicator probe tip 153 into intimate contact with the lower portion 108 of the test tube 107), the sonicator 152 is energized.

Because the test tube 107 is made of a material that is compliant to acoustic energy emitted by the sonicator unit 150, and with the sonicator probe tip 153 being urged against a generally lower portion 108 of the test tube where the sample contents tend to gravitate, the sonic energy emitted by the sonicator probe tip 153 will not only be efficiently transferred through the sidewalls of the test tube, but will be effectively concentrated upon that volume of the test tube containing the particulate of the sample, as shown at 106 in FIG. 9. This concentration of the sonicator's acoustic beam provides for maximum efficiency particle separation and rapid mixing of the sample, surfactant and carrier fluid.

The substantially improved efficiency of acoustic energy coupling of the external sonicator of the invention means that the amount of sonicator drive energy required to achieve thorough mixing of the sample can be significantly reduced, in comparison with the relatively poor efficiency of the immersed probe approach of the prior art, described above. Moreover, since the sonicator of the invention is not immersed into the sample, it does not displace any of the contents of the test tube, and cannot become coated or contaminated thereby. Therefore, the life of the probe is substantially improved, as the probe can be repeatedly reused for successively indexed tube samples, without servicing.

After the fill and sonication mix operations carried out at the filling station 170 are completed, the linear translation units 156 and 158 are again energized, so as to displace the sonicator unit 150 against the bias of the tension springs 161, 162 and away from contact with the test tube, as shown in FIG. 8. The carousel 105 is then indexed to bring the 'sonicated' test tube to a sample dispensing position 180 shown in FIG. 3 as being located circumferentially downstream of the filling station 170. This sample dispensing position is located alongside an opening or slot through the cylindrical sidewall 119 and an opening 185 (shown in FIG. 12) in the floor 115 of the carousel support pan 117. This provides capture access to the test tube 107 by a tiltable capture cradle 181, located adjacent to the sample reception and storage reservoir 101 of the particulate sample analyzer 103.

Figure 10:
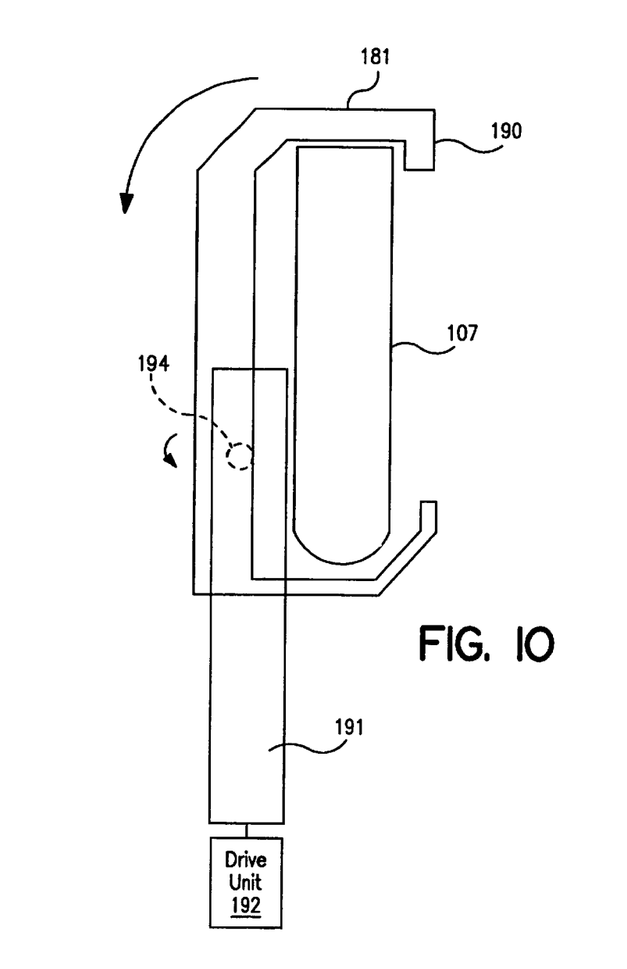
FIGS. 10, 11 and 12 are diagrammatic side views associated with the operation of a tiltable capture cradle.
Figure 11:
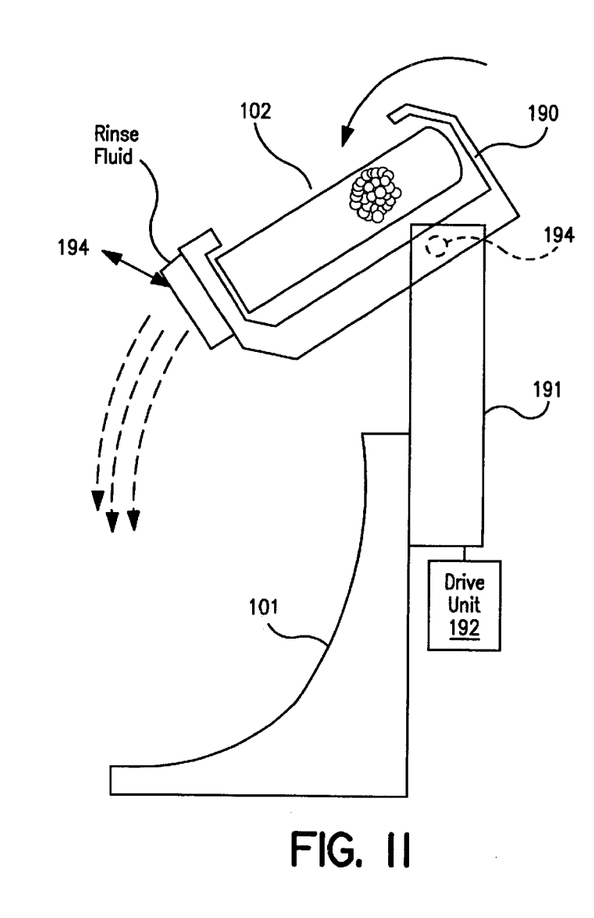
Figure 12:
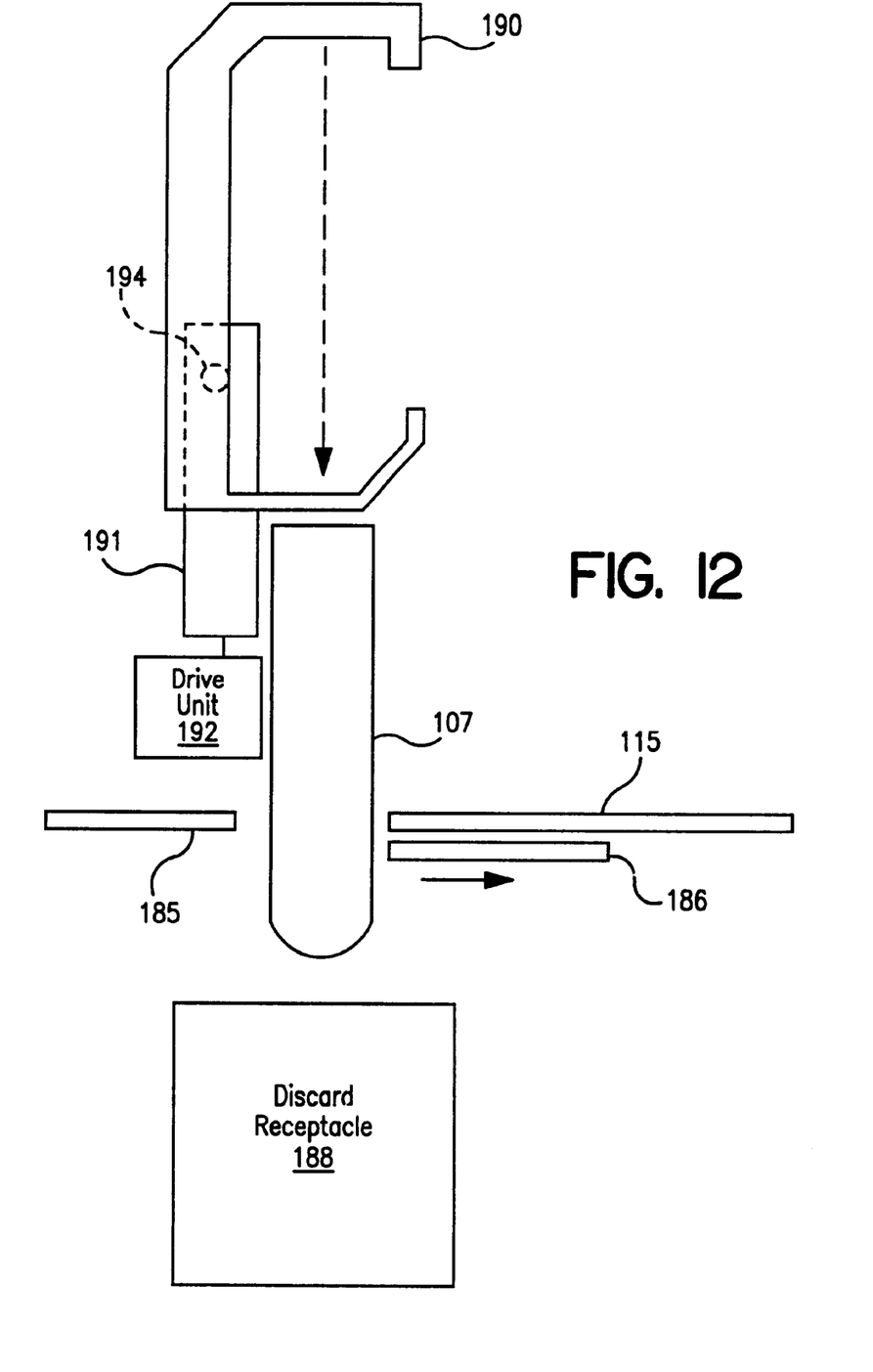

As diagrammatically shown in the side views of FIGS. 10, 11 and 12, the tiltable capture cradle 181 includes a tiltable frame 190 and an associated pivot arm 191 that are sized and configured to receive and retain a test tube in its vertical orientation, as indexed from the filling station 170 by the carousel 105 to the sample dispensing position, on the one hand, and in also a tilted, generally upside down orientation, for dispensing the sonicated contents of the tube. Through an associated drive unit 192 coupled thereto, the cradle is pivoted about a horizontal axis 194, that is located such that, the tube is rotated very quickly from its captured vertical orientation to a below-the-horizontal attitude over the reservoir 101, thereby causing essentially the entire sonicated contents of the tube to be rapidly expelled into the analyzer reservoir. This rapid pivot action is similar to the manner in which an individual would rapidly manually tilt a test tube to an almost upside down position, in order to quickly 'dump' its entire contents at once, rather than effect a more 'gradual' or slow pouring of the contents of the tube, that might otherwise leave a 'trail' of non-dispensed sediment along the interior tube wall.

As shown in FIG. 11, a rinse unit 194 may be coupled with the top end of the cradle 181 and be controllably operated while the tube is in its tilted, sample-dispensing orientation above the reservoir 101. This rinse operation serves to perform an auxiliary carrier 'flush' of the tube, and thereby ensure that its entire contents are fully dispensed into the reservoir. After the sample-dispensing operation, the tube capture cradle 181 is returned by the drive unit 192 to its previous test tube receiving and capture position. As shown in FIG. 12, as the pivot arm 191 moves away from the frame 190, a trap door 186 or the like beneath the opening 185 in the floor 115 of the carousel support pan is opened to allow the test tube 107 to be released by the cradle and drop into a suitable collection or discard receptacle 188.

As will be appreciated by the foregoing description, the above-described shortcomings of conventional particulate sample delivery and mixing devices, including those associated with immersing the sonicator into the fluid contents of the analyzer reservoir, are substantially reduced or eliminated by the particulate sample mixing and delivery apparatus of the invention, which thoroughly externally sonically mixes each sample in its own sequentially indexed storage container prior to being dispensed into the analyzer reservoir. Since the sample container is compliant to acoustic energy, the sonicator unit may be placed against that portion of the container where its sample contents tend to gravitate, whereby the sonic energy emitted by the sonicator probe will be effectively concentrated upon that volume of the test tube containing the particulate of the sample, to provide maximum efficiency particle separation and rapid mixing of the sample, surfactant and carrier fluid, and allow the amount of sonicator drive energy required to achieve thorough mixing of the sample to be reduced. Also, since the sonicator of the invention is not immersed into the sample, it cannot become contaminated or corroded thereby, so that the life of the probe is substantially improved.

While we have shown and described an embodiment in accordance with the present invention, it is to be understood that the same is not limited thereto but is susceptible to numerous changes and modifications as known to a person skilled in the art, and we therefore do not wish to be limited to the details shown and described herein, but intend to cover all such changes and modifications as are obvious to one of ordinary skill in the art.

What is claimed is:

1. A method of processing a sample of material comprising the steps of:
    (a) placing said sample of material into a container being supported in a container support device;
    (b) placing an acoustic energy emitter at an external portion of said container;
    (c) causing acoustic energy to be emitted from said acoustic energy emitter and pass through said container and into said sample of material to sonically mix contents of said sample of material;
    (d) causing relative displacement between said acoustic energy emitter and said external portion of said container; and
    (e) dispensing sonically mixed contents of said sample of material from said container into a reservoir.

2. A method according to claim 1, wherein said container is made of container material that is compliant to acoustic energy emitted by said acoustic energy emitter, step (b) comprises placing said acoustic energy emitter in intimate, acoustic energy-coupling contact with said external portion of said container material, and step (c) comprises causing acoustic energy to be emitted from said acoustic energy emitter, through said container material and into said sample of material.

3. A method according to claim 1, wherein step (a) further includes introducing a carrier fluid into said container, and wherein step (c) comprises causing acoustic energy to be emitted from said acoustic energy emitter, as placed at said external portion of said container, and pass through said container and into contents thereof, so as to sonically mix said sample of material, and carrier fluid.

4. A method according to claim 1, further including the step of:
    (f) disposing of said container.

5. A method according to claim 4, wherein said reservoir is coupled to a sample analysis apparatus, which is operative to analyze contents of said sonically mixed contents of sample of material dispensed therein.

6. A method according to claim 5, said container is one of a plurality of containers containing samples of material transportable by way of a conveyor, and wherein step (b) further includes moving said conveyor so as to transport a respective container containing said sample of material to a location adjacent to said acoustic energy emitter.

7. A method according to claim 6, further including step (g) of repeating steps (b)–(f) for additional containers transportable by said conveyor.

8. An apparatus for processing at least one of a plurality samples of material comprising:
    a conveyor which is configured to transport a plurality of containers containing respective samples of said plurality of samples of material to a sample mixing location;
    an acoustic energy emitter disposed at said mixing location and being configured to engage an external portion of a respective container that has been transported to said mixing location by said conveyor, and to emit acoustic energy through said respective container and into sample material therein, sonically mixing contents of sample material; and
    a device for orienting said respective container for dispensing mixed contents thereof into a reservoir, and then for disposing of said container.

9. An apparatus according to claim 8, wherein each of said containers is made of container material that is compliant to acoustic energy emitted by said acoustic energy emitter, and wherein said acoustic energy emitter is mechanically biased against said respective container when emitting acoustic energy through said respective container and into sample material therein.

10. An apparatus according to claim 9, wherein said acoustic energy emitter is arranged to be urged against a generally lower portion of said respective test tube.

11. An apparatus method according to claim 8, further including a device for introducing carrier fluid into said respective container, and wherein acoustic energy emitted from said acoustic energy emitter passes through said respective container and into contents thereof, so as to sonically mix said sample of material, and carrier fluid.

12. An apparatus according to claim 8, wherein said reservoir is coupled to a sample analysis apparatus, which is operative to analyze contents of said sonically mixed contents of said container dispensed therein.

13. An apparatus for processing a plurality samples of material comprising:
    a conveyor which is configured to transport a plurality of containers made of container material that is compliant to acoustic energy and containing respective samples of said plurality of samples of material to a sample filling and mixing location;
    a device disposed at said sample mixing and filling location, which is operative to introduce carrier fluid and surfactant into a respective container;

an acoustic energy emitter disposed at said mixing location and being positioned adjacent an external portion of said respective container that has been transported to said mixing location by said conveyor, and to emit acoustic energy through said respective container and into contents thereof, so as to sonically mix said sample of material, carrier fluid and surfactant; and a device for orienting said respective container, so as to dispense mixed contents thereof into a reservoir, and then to dispose of said container.

14. An apparatus according to claim 13, wherein said conveyor comprises a controllably indexed carousel, that is driven by a releasable clutch, and is operative to rotationally transport each of said plurality of containers containing respective samples of material to said mixing and filling location, and wherein said acoustic energy emitter comprises a radially translatable sonicator unit supported adjacent to said carousel and including a generally longitudinal probe element, and a controllable bias arrangement coupled to said sonicator unit and being operative to controllably bias a probe tip of said sonicator unit toward or away from intimate contact said respective container that been indexed by said carousel to said mixing and location.

15. An apparatus according to claim 14, wherein said carousel is operative to transport said respective container to a sample dispensing position downstream of said mixing and filling location, and wherein said device for orienting said respective container, so as to dispense mixed contents thereof into a reservoir comprises a tiltable capture cradle adjacent to a reservoir of a sample analyzer.

16. A device for mixing a sample of material in a container, the device comprising:

a sonicator unit comprising an acoustic energy emitting probe that is positioned adjacent an exterior surface of the container that is compliant to acoustic energy emitted by said acoustic energy emitting probe for sonically mixing said sample of material provided therein; and a device for orienting said container for dispensing mixed contents thereof into a reservoir, and then for disposing of said container.

17. A device according to claim 16, wherein said container is made of an elastically deformable material that is complaint to acoustic energy emitted by said sonicator unit, and wherein said device is further operative to introduce a carrier fluid into said container, so that acoustic energy emitted from said sonicator sonically mixes said sample of material, and carrier fluid.

18. A method of processing a sample of material comprising the steps of:

(a) placing said sample of material, a carrier fluid and a surfactant into a container that is compliant to acoustic energy emitted by an acoustic energy emitter;

(b) placing an acoustic energy emitter at an external portion of said container;

(c) sonicating said sample of material with the carrier fluid and the surfactant prior to dispensing said sample material into a sample receptacle of a sample analysis apparatus, which is operative to analyze contents of sonically mixed contents of the sample of material;

(d) causing relative displacement between said acoustic energy emitter and said external portion of said container; and (e) dispensing said sample of material as sonicated with said carrier fluid and surfactant in step (c) into said sample receptacle of the sample analysis apparatus.

19. A method according to claim 18, wherein step(c) comprises causing acoustic energy to be emitted from said acoustic energy emitter, as placed at said external portion of said container, and pass through said container and into contents thereof, so as to sonically mix said sample of material, carrier fluid and surfactant.

* * * * *